(12) United States Patent
Havel et al.

(10) Patent No.: US 10,314,560 B2
(45) Date of Patent: Jun. 11, 2019

(54) OVER-THE-WIRE ULTRASOUND SYSTEM

(71) Applicant: Muffin Incorporated, West Lafayette, IN (US)

(72) Inventors: William J. Havel, West Lafayette, IN (US); Sarah Robbins, Lafayette, IN (US); Peter S. McKinnis, West Lafayette, IN (US); Yun Zhou, West Lafayette, IN (US); Neal E. Fearnot, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 840 days.

(21) Appl. No.: 14/501,746

(22) Filed: Sep. 30, 2014

(65) Prior Publication Data

US 2015/0094595 A1     Apr. 2, 2015

Related U.S. Application Data

(60) Provisional application No. 61/885,155, filed on Oct. 1, 2013.

(51) Int. Cl.
| A61B 8/00 | (2006.01) |
| A61B 8/08 | (2006.01) |
| A61B 8/12 | (2006.01) |
| A61B 1/018 | (2006.01) |

(52) U.S. Cl.
CPC ............ *A61B 8/0891* (2013.01); *A61B 1/018* (2013.01); *A61B 8/12* (2013.01); *A61B 8/445* (2013.01); *A61B 8/4461* (2013.01); *A61B 8/4444* (2013.01)

(58) Field of Classification Search
CPC ......... A61B 1/018; A61B 8/0891; A61B 8/12; A61B 8/4444–8/4461
See application file for complete search history.

(56) References Cited

U.S. PATENT DOCUMENTS

| 4,732,156 A | * | 3/1988 | Nakamura | ............... | A61B 8/12 |
| | | | | | 600/101 |
| 4,834,102 A | | 5/1989 | Schwarzchild et al. |
| 5,176,141 A | | 1/1993 | Bom et al. |
| 5,181,514 A | * | 1/1993 | Solomon | .................. | A61B 8/12 |
| | | | | | 600/152 |
| 5,318,532 A | | 6/1994 | Frassica |

(Continued)

FOREIGN PATENT DOCUMENTS

| CN | 103037772 A | 4/2013 |
| JP | H03-165781 | 7/1991 |

(Continued)

OTHER PUBLICATIONS

English Translation of JP Office Action for 2016-519807.

(Continued)

*Primary Examiner* — Angela M Hoffa
*Assistant Examiner* — Vani Gupta
(74) *Attorney, Agent, or Firm* — Woodard, Emhardt, Henry, Reeves & Wagner, LLP

(57) ABSTRACT

Disclosed are embodiments of devices and methods for imaging the inside of a body part, such as a blood vessel. In particular embodiments, a catheter has a chamber within which is a transducer. A wire guide channel extends throughout the length of the catheter. The transducer is rotatable around the wire guide channel.

20 Claims, 9 Drawing Sheets

(56) References Cited

U.S. PATENT DOCUMENTS

| | | | |
|---|---|---|---|
| 5,357,963 A * | 10/1994 | Mayol | A61B 8/10 600/446 |
| 5,377,682 A * | 1/1995 | Ueno | A61B 8/12 600/446 |
| 5,377,685 A | 1/1995 | Kazi et al. | |
| 5,479,929 A * | 1/1996 | Cooper | A61B 8/12 600/459 |
| 5,799,655 A | 9/1998 | Jang et al. | |
| 5,846,204 A * | 12/1998 | Solomon | A61B 8/0883 600/463 |
| 6,200,269 B1 | 3/2001 | Lin et al. | |
| 6,599,288 B2 | 7/2003 | Maguire et al. | |
| 6,607,502 B1 | 8/2003 | Maguire et al. | |
| 7,798,971 B2 | 9/2010 | Flesch et al. | |
| 2002/0022833 A1 * | 2/2002 | Maguire | A61B 17/2202 606/27 |
| 2002/0143252 A1 * | 10/2002 | Dunne | B06B 1/04 600/437 |
| 2005/0283080 A1 | 12/2005 | Nita et al. | |
| 2007/0088213 A1 * | 4/2007 | Poland | G01S 7/52084 600/437 |
| 2007/0239010 A1 | 10/2007 | Johnson | |
| 2008/0177183 A1 | 7/2008 | Courtney et al. | |
| 2009/0030312 A1 | 1/2009 | Hadjicostis | |
| 2009/0131798 A1 * | 5/2009 | Minar | A61B 5/02007 600/463 |
| 2010/0249601 A1 | 9/2010 | Courtney | |
| 2011/0166455 A1 | 7/2011 | Cully et al. | |
| 2011/0263986 A1 * | 10/2011 | Park | A61B 8/12 600/462 |
| 2014/0107489 A1 * | 4/2014 | Fearnot | A61B 8/12 600/463 |
| 2014/0194743 A1 | 7/2014 | Havel et al. | |
| 2016/0374751 A1 * | 12/2016 | Davies | A61B 18/1477 606/48 |

FOREIGN PATENT DOCUMENTS

| | | |
|---|---|---|
| JP | H05-076530 | 3/1993 |
| JP | H05-228149 | 9/1993 |
| JP | H07-136171 | 5/1995 |

OTHER PUBLICATIONS

Machine Translation of CN103037772 A, retrieved from Total Patent on Aug. 15, 2018.

Machine Translation of JP 07-136171, obtained Jun. 5, 2018 from European Patent Office Patent Translate, 12 pages.

Machine Translation of JP H05-228149, obtained Jun. 5, 2018 from European Patent Office Patent Translate, 10 pages.

U.S. Pat. No. 5,318,532 Corresponding to JP H03-165781.

U.S. Pat. No. 5,377,682 Corresponding to JP H05-076530.

* cited by examiner

OVER-THE-WIRE ULTRASOUND SYSTEM

CROSS-REFERENCE TO RELATED APPLICATION

This application claims the benefit of U.S. Provisional Application No. 61/885,155 filed Oct. 1, 2013, which is hereby incorporated by reference.

FIELD OF THE DISCLOSURE

The present disclosure concerns devices and methods for ultrasound use within the human body, including devices and methods for employing ultrasound in body areas such as the interior of blood vessels for imaging or therapeutic applications.

BACKGROUND

Ultrasound technology has been used for therapeutic and diagnostic medical procedures, which can include providing imaging of internal portions of a body. For example, devices have been proposed for ultrasound imaging within blood vessels to view the condition of the vessel and/or placement or condition of a device placed in the vessel, as well as to help to determine plaque volume and the degree of stenosis within an artery lumen. That information is often difficult to obtain through angiographic imaging and exterior ultrasound imaging, particularly in regions having multiple overlapping arterial segments.

In some examples of intraluminal ultrasound procedures, a catheter is fitted with a transducer. A wire guide is positioned within a body conduit through use of angiography or ultrasound and is used to safely direct the catheter through the anatomy. The catheter is slid over the wire guide and positioned near the farthest end of the wire guide. The transducer transmits and/or receives ultrasound waves.

Difficulties arise in constructing adequate catheters having transducers in very small sizes in order to safely reach particular body conduits, such as for example with intravascular applications. Problems with existing two dimensional designs include wire guide channels which block a portion of the acoustic window. Additionally, wire guide channels take up valuable space in the catheter that could otherwise be used by ultrasound hardware. Three options for transducers that can be fitted into a catheter each have their own difficulties when compared to an external ultrasound device.

The first option is a single element transducer. The size of a single element transducer is typically appropriate for body conduits (for example 1-2 mm diameter) and the sensitivity or signal-to-noise ratio is good. Single element transducers are limited because they require a mechanical rotating mechanism, have a fixed focus, and require a slip ring or rotary transformer which adds cost. Existing catheters with this design do not have over-the-wire or rapid exchange capability.

The second option is a linear or phased array which includes multiple elements with the elements aligned in an axial direction. Advantages of this option are that the transducer is very flexible and acoustic performance is usually good. It also does not require mechanical rotation. Disadvantages are that it does not provide 360° side-view imaging. The cost is usually higher than a single element transducer and it requires more coaxial cables which can add bulk and complexity. This presents particular problems for over-the-wire designs or rapid exchange designs as there is not much space available within the catheter.

The third option is a circular array transducer having multiple elements that are all side-facing. A circular array design does not require mechanical rotation, provides 360° cross sectional imaging, and the cost is typically similar to single element transducer designs. This design is particularly suited for over-the-wire or rapid exchange designs, however the imaging quality suffers compared to other designs.

Other problems exist in current catheter configurations. For example, many such devices provide at best an image of a cross section of tissue or other items of interest, i.e. a thin, disk-shaped slice of the interior of a body conduit with a portion in the center that is not within the range of the ultrasound beam. In some other devices, the ultrasound beam is directed at a fixed angle that is not substantially perpendicular to the longitudinal axis (e.g. at 45 degrees). In this case the imaged region is static and takes the form of a truncated portion of the surface of a cone. In either case, in order to visualize the entirety of a significant length within the body (e.g. surfaces or portions of tissue, or of devices), the device must be moved along that length, with respective images of cross sections taken at particular locations. Such movement may be inexact, and may include risks associated with blind insertion of the device through the vessel, as well as being slow. Typical pull back images take on the order of 30 seconds to perform (at a speed of about 0.1 mm/second). Additionally, any changes in the orientation of the transducer during pullback distort the image.

Three-dimensional information provides added value useful for navigation and confirmation of position of devices within body conduits. In an intravascular example, catheters can be moved within vessels and the image data obtained via ultrasound can be combined or otherwise processed in order to create 3D information. A limitation of this technique is that it does not provide real-time information, so it cannot help with device delivery, but rather assists only with assessment of the device placement after delivery. Additionally, the catheter tip motion and angle must be known in order to produce accurate and usable data.

Three-dimensional images may be acquired by one-dimensional arrays connected to a mechanical actuator which moves the arrays within the catheter or other device. Such designs are expensive and generally require more space in a device than many vessels will permit. To achieve good image quality, such array transducers must simultaneously transmit and receive on many separate channels. That condition requires many expensive and bulky coaxial cables. Fewer coaxial cables can be used, but doing so reduces the quality of the image and image frame rate.

Ultrasound devices have been proposed which include a motion of a transducer about two axes to provide 3D information. However, in many devices the mechanical mechanisms that provide such movement tend to be bulky and require dimensions which are unsuitable for applications in catheters or small body areas. These problems are magnified when attempting to place a wire guide channel within the catheter. Proposed 3D or forward-looking transducer systems that are over the wire include a ring-array of very small transducer elements around the catheter lumen. However, such designs involve complex connections in small spaces which are accompanied by problems with wiring, cost and manufacturing. As a result, the connections are typically minimized and the image quality suffers accordingly.

There remains a need for a catheter placeable over a wire guide which can provide accurate and efficient application of ultrasound in three dimensions along a substantial length of a small body conduit. There also remains a need for such a device that can view a medical device and one or more tissues or tissue parts simultaneously, particularly in cases in which the device and tissue(s) could not have been imaged reliably in any two-dimensional plane.

SUMMARY

Among other things, disclosed is a device and methods for providing an internal ultrasound capability over a wire guide. In one example, a device includes a housing and a transducer positioned within the housing. The transducer is rotatable relative to the housing along a rotation path about a rotation axis. The device includes a wire guide channel, a portion of which is positioned substantially parallel to the rotation axis and radially inward of the most radially outer extent of the rotation path. The channel is sized and configured to receive a wire guide and extends through the length of the device. In one example, the transducer is a single element transducer rotatable about a single axis for 2D imaging. In another example, the transducer is a linear array transducer rotatable about a single axis for 3D imaging. In another example, the transducer is rotatable about two axes and configured for 3D imaging. In that case, the transducer includes a first element and a second element. The first element is positioned opposite to the second element with respect to the rotation axis so that the channel extends between the first element and the second element.

The 3D imaging device includes a pivot mechanism rotatable about the rotation axis and a pivot member mounted to the pivot mechanism and pivotable about a pivot axis that is substantially perpendicular to the rotation axis with the transducer being included in the pivot member. The second element is connected to the first element so that the second element pivots about the pivot axis in response to pivoting motion of the first element.

The device includes a motor having a shaft extending substantially along the rotation axis such that operation of the motor rotates the shaft around the rotation axis. The shaft includes a conduit and the channel extends through the conduit. The transducer is rotatable through a range defining an acoustic window extending from the transducer so that the entire acoustic window is substantially echolucent, i.e. having very low acoustic attenuation and/or having acoustic impedance that matches blood or water.

The transducer portion of the channel extends from a control side of the transducer past the transducer to at least an application side of the transducer. The transducer portion is in fluid communication with an area external to the housing. The transducer portion of the channel is defined by a cannula. The cannula is substantially echolucent. The channel is positioned substantially parallel to the rotation axis and radially inward of the most radially inward extent of the rotation path.

In some examples, the housing includes a tubular member for containing the transducer. The tubular member has a chamber defined at least in part by a wall portion of the tubular member. The chamber houses at least the transducer and the medium. The wall portion and the medium have similar acoustic impedance to the part of the body into which the tubular member is inserted so that reflection of ultrasound at the boundary of the medium and the wall portion and at the boundary of the wall portion and body environment is reduced to a level acceptable for imaging through the housing. In some examples, the tubular member is a catheter.

In some examples the pivot member includes a magnetic layer. The device includes a coil positioned concentric to the rotation axis. The coil includes a plurality of electrically conductive windings. Application of electric current to the coil creates a torque on the pivot member about the pivot axis. A motor having a rotatable shaft extends substantially along the rotation axis such that operation of the motor rotates the shaft around the rotation axis. The shaft includes a conduit and the channel extends through the conduit.

In some examples the device includes a rotatable shaft extending substantially parallel to the rotation axis and rotatable about the rotation axis. The shaft includes a conduit extending therethrough. The wire guide channel extends through the shaft. The transducer is operatively coupled with the rotatable shaft so that it rotates in response to rotation of the shaft.

A transducer portion of the channel extends from a control side of the transducer past the transducer to at least an application side of the transducer such that the transducer portion is in fluid communication with an area external to the housing. The transducer portion of the channel is defined by a cannula. In some examples, the cannula is constructed of a material that is acoustically transparent and/or the cannula is sized to accommodate a wire guide having a diameter between 0.01 inches to 0.038 inches.

In some examples the device has a motor for driving the rotatable shaft such that operation of the motor rotates the shaft around the rotation axis. The device includes a conduction path which includes a slip ring. The conduction path extends between the transducer and a control side of the transducer. The transducer includes an array of elements configured for 3D imaging. The housing further comprises a wall having an inner surface such that the rotation path is between the wire guide channel and the inner surface.

Further forms, objects, features, aspects, benefits, advantages, and embodiments of the present disclosure will become apparent from a detailed description and drawings provided herewith.

DESCRIPTION OF THE SELECTED EMBODIMENTS

Figure 1:
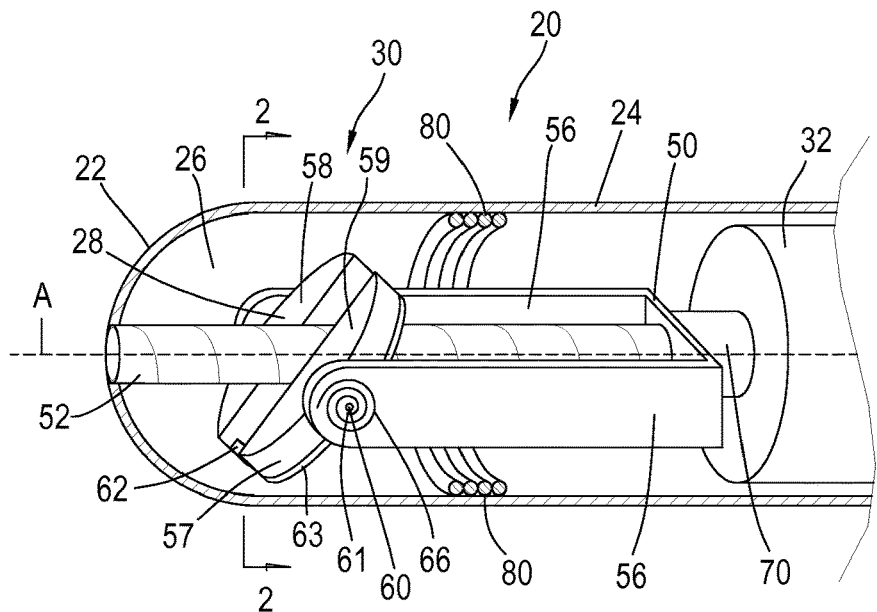
FIG. 1 is an illustrative perspective view of an embodiment of a 3D imaging ultrasound device having a split transducer, a pivot member, a motor shaft, and a wire guide passageway.

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the disclosure relates. One or more embodiments are shown and described in detail, although it will be apparent to those skilled in the relevant art that some features that are less relevant may not be shown for the sake of clarity.

Referring now generally to the drawings, shown are exemplary embodiments of a device 20 for internal ultrasound procedures. Such devices may be diagnostic or therapeutic (including interventional) in application, and include devices inserted percutaneously, subcutaneously or endoluminally into the patient. Device 20 can be used with a system which includes a console (not shown) for processing data or signals received from an ultrasound transducer. The ultrasound console can be a type which is generally used for medical ultrasonic imaging, e.g. generally including control devices usable by a physician and a graphic display which displays graphical images obtained during an ultrasound procedure. The device 20 is connectable to the console portion through standard connections. Device 20 can be used for obtaining images at various locations and conduits of a body such as a blood vessel, urethra, ureter, vagina, rectum, throat, ear, or through an artificial tract by percutaneous puncture for example. Device 20 is capable of transmitting and receiving ultrasound signals and then communicating data obtained from ultrasound signals to the console.

In the embodiment shown schematically in FIG. 1, device 20 includes a catheter 22 or other flexible elongated or tubular member having a wall 24. Wall 24 has an inner surface defining an internal chamber 26, within which is included a transducer 28, a pivot mechanism 30, a motor 32, a cannula 52, and a coil 80. Catheter 22 is sized and configured for insertion into and/or travel along bodily orifices or lumens. Cannula 52 forms a portion of a wire guide channel extending through the catheter. As will be discussed further below, pivot mechanism 30 allows transducer 28 to be turned around a rotation axis (axis A) of device 20 as well as pivoted around a pivot axis substantially perpendicular to the rotation axis. This allows the direction of ultrasound emission and reception to extend forward (axially relative to the rotation axis) and laterally (radially relative to the rotation axis). In the illustrated embodiments, the rotation axis is the longitudinal axis (i.e. extending axially through catheter 22) of device 20, and the pivot axis is a lateral axis (e.g. perpendicular to the longitudinal axis). Transducer 28 in conjunction with motor 32 and pivot mechanism 30 is capable of transmitting and receiving ultrasound signals in a variety of directions or orientations which are passed along data signal communication lines between transducer 28 and the ultrasound console.

Catheter 22 in the illustrated embodiment is an elongated device of plastic or other sturdy flexible material. Catheter 22 includes a control end which during use is nearest to the user and an application end positioned opposite to the control end. The terms "control" and "application" are used throughout this description to describe the relative positions between parts of catheter 22, and more generally device 20. As an illustrative example, if an exemplary part A is described as being positioned on the control side of an exemplary part B, then the exemplary part A is positioned closer to the control end along catheter 22 compared to the exemplary part B.

Wall 24 surrounds chamber 26, which is at or near the application end of device 20 in the illustrated embodiment. The control end of wall 24 and/or catheter 22 may extend outside of the patient during use, or may attach to another piece that extends outside the patient, and may end in a handle or other operating portion for maneuvering catheter 22. The application side end of catheter 22 is formed as a dome in some embodiments.

Cannula 52 is an elongated structure having a lumen and constructed of plastic or other sturdy flexible material. Cannula 52 forms at least part of a wire guide channel which extends throughout the length of the catheter. As used throughout this description, the wire guide channel is a continuous passageway (or lumen) extending from the control side end of the catheter to the application side end of the catheter. In various embodiments, portions of the wire guide channel are defined by a cannula, a motor shaft, a mounting piece, a wall portion of catheter 22, or other structures as described herein. The wire guide channel extends generally along the rotation axis in the illustrated embodiment, particularly with respect to the application side of catheter 22.

As used herein, the term "mounting piece" refers to types of frames or structures that support a transducer. Various embodiments of the mounting piece can allow rotational motion of the transducer around a rotation axis, house beamforming circuitry, define part of a wire guide channel, and/or include a cavity for housing a transducer element as well as providing other features or functions as described herein.

Cannula 52 as shown extends generally along the rotation axis. In some embodiments, cannula 52 has an axial center which is aligned with the rotation axis. In other embodiments cannula 52 has an axial center which is offset from the rotation axis in some portions or along the entire length of cannula 52. The wire guide channel (and correspondingly cannula 52) is sized to receive at least a wire guide so that the wire guide can be fed through catheter 22 and out the application end of catheter 22. The wire guide channel can be configured to accept varied sizes of wire guides, such as wire guides with diameters between 0.01" and 0.038" for example. In some embodiments, cannula 52 extends throughout the length of the catheter and forms the entirety of the wire guide channel. In other embodiments, cannula 52 forms a portion of the wire guide channel (e.g. the application side end of the wire guide channel). In other embodiments, multiple cannulas (including cannula 52) form all or portions of the wire guide channel. Cannula 52 extends to or through a hole in wall 24 at the furthest application side end of catheter 22. In some embodiments, cannula 52 extends through wall 24 a sufficient distance to sealingly engage with wall 24, but cannula 52 generally does not extend past the outer surface of wall 24 to prevent cannula 52 from creating sharp edges or hazards at the end of catheter 22. In that way, the wire guide channel extends through the application end of catheter 22 while maintaining a blunt tip. Cannula 52 sealingly engages with wall 24 so that chamber 26 is sealed from the external environment even while the wire guide channel is fluidly connected with the external environment.

Catheter 22 and cannula 52 both have at least a portion that presents a minimal barrier to the passage of ultrasound signals so that ultrasound images of surrounding matter (e.g. tissue(s) or implant(s)) may be reasonably acquired through the barrier. Catheter 22 and cannula 52 each have at least a portion that is constructed of a material which is substantially echolucent (i.e. having small ultrasound attenuation, having similar acoustic impedance or small differences in acoustic impedance with the surrounding environment) when placed in the surrounding working environment, such that it acts as an acoustic window. It will be understood that only the application end of catheter 22 (e.g. wall 24) and cannula 52 need be acoustically transparent, but more or all of catheter 22 and cannula 52 may be made of the same material in some embodiments. For example, when used within a body conduit containing body tissues and blood, it is preferable for catheter 22 and cannula 52 to be constructed of a material which is structurally rigid and which has acoustic impedance similar to that of body fluids such as blood. Possible materials could include, for example, a polymer material such as high density polyethylene, polymethylpentene (PMP), or acrylonitrile butadiene styrene (ABS). It has been determined that in some cases the thickness of at least the portion of catheter 22 which is positioned within the acoustic window can be approximately N/2 (where N is a positive integer) of the wavelength corresponding to the center frequency of the ultrasound signal.

Particular embodiments of catheter 22 or at least chamber 26 are cylindrical, and are sized for insertion into and passage through body conduits, such as insertion into the femoral artery and passage through it toward the heart. Wall 24 may have a port or other feature to allow injection of a coupling fluid (e.g. saline, oils, or alcohols) into chamber 26 to give chamber 26 ultrasound characteristics similar or substantially identical to that of wall 24 and the surrounding bodily environment (e.g. the blood stream). A bearing or other sealing member (not shown for the sake of clarity) can be placed between motor 32 and transducer 28 (or the portion of chamber 26 containing transducer 28 and a fluid) in some embodiments.

In the FIG. 1 embodiment, transducer 28 is mounted in pivot mechanism 30 to permit transducer 28 to turn around the rotation axis as well as pivot around the pivot axis. Such two-axis movement is capable of providing 3D imaging. In the illustrated embodiments, pivot mechanism 30 is a two-axis gimbal or gimbal-type mounting (or yoke), having a pivot member 57 (including transducer 28), a base 50, and matching arms 56 (or furcations) extending from base 50. Base 50 accommodates a shaft 70 from motor 32, so that motor 32 can turn pivot mechanism 30 around the rotation axis. A pivot member 57 is mounted via holes 60 to arms 56.

In one embodiment, shafts (not shown) are attached to pivot member 57 and fit into holes 60 to act as axles, so that pivot member 57 can pivot around the pivot axis defined by the shafts. Other gimbal structures could be used which provide pivoting (or elevational) rotational motion to the transducer, examples of which are explained in U.S. Patent Application Ser. No. 61/713,172 and WO 2014/059292, each entitled "Devices and Methods for Three-Dimensional Internal Ultrasound Usage" and which are incorporated herein by reference in their entirety.

Figure 2:
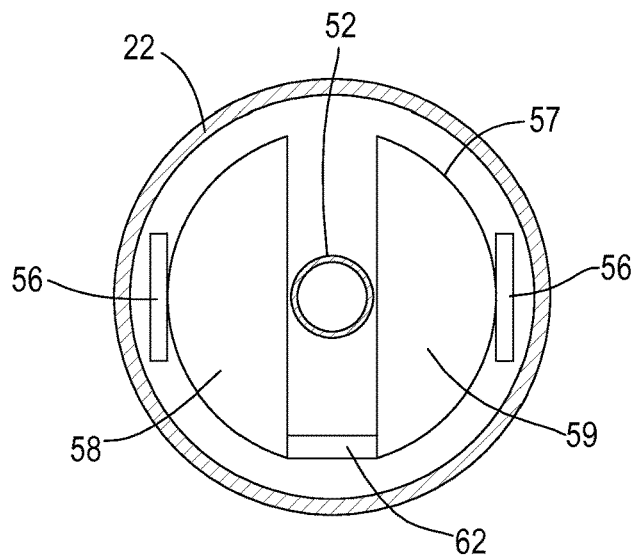
FIG. 2 is an illustrative cross-sectional front view of an end of an embodiment of the ultrasound device of FIG. 1 showing the pivot member.

Pivot member 57 in the illustrated embodiment includes two sections 58, 59. Sections 58 and 59 are generally shaped as halves (or portions) of a circular disc (see FIG. 2). A connector 62 connects section 58 to 59 so that section 58 rotates in response to rotation of section 59 about the pivot axis and vice versa. In other words, sections 58 and 59 are rotatable together or in unison about the pivot axis. Connector 62 attaches an end of section 58 to an end of section 59. In other embodiments, a second connector (not shown) can connect the opposite ends of sections 58 and 59. Section 58 is spaced apart from section 59 to accommodate cannula 52 which extends between section 58 and section 59. Pivot member 57 is therefore rotatable through a path (or rotation path) over cannula 52 (and its wire guide path) about both the pivot axis and the rotation axis. In other words, the wire guide channel is positioned substantially parallel to the rotation axis and radially inward of the most radially outer extent of the path. Similarly, in some embodiments the wire guide channel is positioned substantially parallel to the rotation axis and radially inward of the most radially inward extent of the path.

In the illustrated embodiment, the range of rotation of pivot member 57 about the pivot axis is bounded by abutment of connector 62 against cannula 52. In some embodiments (not shown) connector 62 is shaped to modify the range of rotation of pivot member 57 about the pivot axis. For example, connector 62 can be shaped generally as a curve (e.g. a u-shape) so that pivot member 57 can reach a maximum angular displacement in which the viewing angle of transducer 28 is generally perpendicular to the rotation axis. Similarly, the attachment points of connector 62 to sections 58 and 59 can be moved to modify the range of rotation. In this way, pivot member 57 is free to rotate through a range of about 180 degrees, or about 90 degrees in either direction until connector 62 abuts against cannula 52. In other embodiments, one or more connectors 62 could be configured and positioned to bound the rotational range of pivot member 57 to about 90 degrees, or between a position in which the viewing angle of transducer 28 is substantially parallel to the rotation axis and a position in which the viewing angle of transducer 28 is substantially perpendicular to the rotation axis.

One or more bias members 66 bias pivot member 57 to a particular initial resting or neutral position. In the illustrated embodiment, bias member 66 is a torsion spring connected to an arm 56 at or toward one end, and to a shaft or pivot member 57 at the other (e.g. by inserting an end of bias member 66 into a groove in a shaft which connects pivot member 57 to arm 56). The torsion spring is a helically shaped spring; although other spring types are suitable and can be arranged differently relative to pivot member 57 and arms 56. A second bias member 66 (not shown) may be similarly attached to the other arm 56 and a shaft or pivot member 57. In a particular embodiment, when in the neutral position (not shown) transducer 28 is oriented substantially along the rotation axis; e.g. transducer 28 has a viewing angle which is substantially aligned with the rotation axis with pivot member 57 generally normal to the rotation axis. In other embodiments, the neutral position can be different, for example a position with the viewing angle substantially perpendicular to the rotation axis.

As previously noted, in the illustrated embodiment, transducer 28 is included in pivot member 57. In the illustrated embodiment, transducer 28 is a split single element transducer having one element on section 58 and another element on section 59 so that the two elements are positioned generally opposite from each other with respect to the rotation axis. Transducer 28 is indicated schematically in the drawings. The term "transducer" should be understood to include an assembly of two or more parts as well as a single piece. It will further be understood that "transducer" as used herein includes devices that transmit ultrasound signals (i.e. transform an electrical (RF) signal to ultrasound), receive ultrasound signals (i.e. transform ultrasound to an electrical (RF) signal), or both. Transmission of ultrasound may occur at one element of transducer 28 and reception at another element of transducer 28. Transducer(s) as described herein may have one or more piezoelectric elements as respective transducers, and may operate in combination with other transducers within or outside the body. As examples, "transducer" as used herein includes a split single element transducer on a rotating and pivoting member, a single element transducer on a rotating and pivoting member, or a one-dimensional array of elements on a rotating and/or pivoting member.

Figure 13:
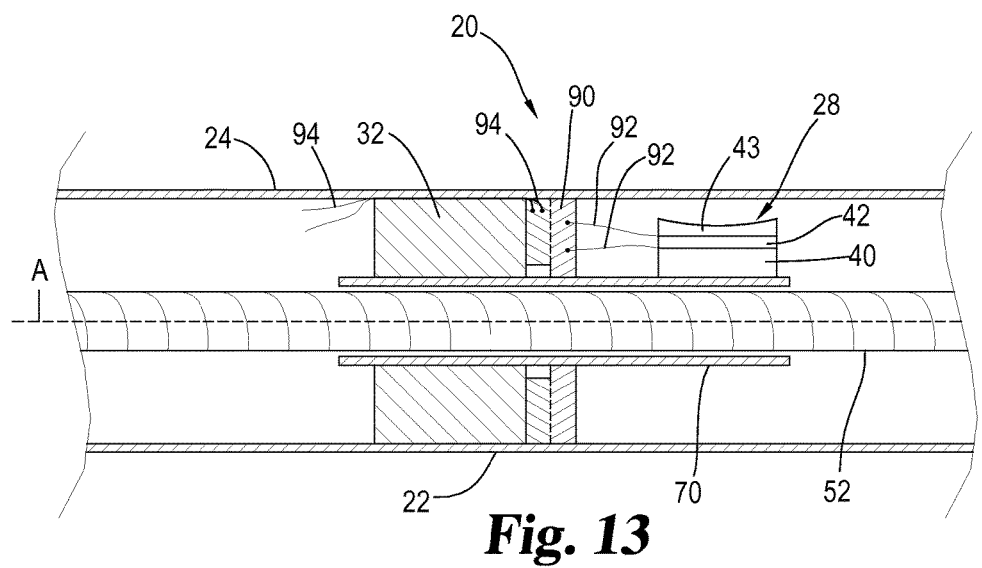
FIG. 13 is an illustrative view of a portion of an alternative embodiment of the ultrasound device having a single element rotating transducer.

An exemplary transducer 28 as used in the embodiments described herein includes a backing 40, one or more ultrasound elements 42, and a matching layer 43. An exemplary transducer 28 showing the various parts of transducer 28 is shown in FIG. 13, although the discussion herein of transducer 28 applies also to the other embodiments described herein. At least one ultrasound element 42 is attached to, positioned adjacent to, or positioned near to one side of backing 40. In the FIG. 1 embodiment, one or both sections 58, 59 can include a transducer 28. Matching layer 43 is attached to one side of element 42. In some embodiments, element 42 can be focused by attaching matching layer 43 and then curving element 42 or by adding an acoustic lens (for example, a rubber lens) on top of matching layer 43.

In some embodiments, element 42 is a piezoelectric element which has the ability to convert electrical energy into sound waves and sound waves into electrical energy. The positioning of element 42 as indicated, on a side of backing 40, results in a directed ultrasound beam direction. Backing 40 is any layer positioned adjacent to element 42 that has acoustic impedance that is different from the acoustic impedance of transducer element 42. In various embodiments, backing 40 can have differing designs and functions. Various parameters of the transducer such as resolution, sensitivity, and intensity can be controlled by tailoring the acoustic impedance (i.e. material selection) and size of backing 40. To emphasize resolution, an absorption backing is preferable and is usually made by a material with medium to high acoustic impedance and high attenuation. To emphasize sensitivity, a low acoustic impedance backing is preferable, which can reflect more energy towards the matching layer side of element 42. A transducer designed for therapeutic use requires the ability to generate high-intensity ultrasound signals, in which case backing 40 can be a material having low acoustic impedance compared to element 42. Although backing 40 is generally depicted as part of the transducers disclosed herein, backing 40 is optional in some cases.

When element 42 is energized to create an acoustic signal, a portion of the signal is dampened in backing 40 due to the acoustic impedance of backing 40 and the mismatch compared to the acoustic impedance of element 42. The mismatch allows for a certain amount of damping of the acoustic signal within backing 40 so that such acoustic signals are effectively only projected outward from element 42 through the matching layer side of transducer 28. The matching layer has acoustic impedance generally between that of element 42 and the medium surrounding transducer 28 in order to minimize mismatched acoustic impedance between transducer 28 and the medium surrounding transducer 28. Transducer 28, as discussed, can be a single element transducer which is capable of sending and receiving ultrasound waves in a range of frequencies which are typically used in medical ultrasound procedures, such as, for example, in the range from 20 KHz to 100 MHz. In some examples, transducer 28 can include a linear array of elements extending along the rotation axis or positioned within pivot member 57.

Pivot member 57 also includes a magnetic layer 63, which can be part of section 58, section 59, or both sections 58 and section 59. Magnetic layer 63 is positioned adjacent to or integral with backing 40 in the illustrated embodiment. Magnetic layer 63 may be a permanent magnet attached to transducer 28 adjacent or near to backing 40. Alternatively, magnetic layer 63 could be incorporated into a mounting piece. In other embodiments, a magnet or magnetic material may be integrated with the backing layer as a composite or other method. In some embodiments, magnetic layer 63 is a permanent diametric magnet constructed in the same shape as one or both sections 58 and 59 with the poles aligned with the viewing angle of transducer 28, in which a pole axis running through the north and south poles is generally perpendicular to the pivot axis.

In particular embodiments, pivot member 57 is a body, base, piece, or substrate on which backing 40 (or transducer 28) is fixed and which provides a rotatable coupling with shaft 70. In other embodiments, backing 40 may include shafts to engage with holes 60. In other embodiments, a separate axle may be provided with pivot mechanism 30 to which backing 40 or the magnetic layer is directly or indirectly fixed. Pivot mechanism 30 permits transducer 28 to turn around the rotation axis, via transmission of rotational motion from motor 32 to pivot mechanism 30, and to turn transducer 28 about the pivot axis at the same time, via pulling or pushing force on magnetic layer 63 to move it around the pivot axis. Pivot member 57 is thus able to rotate about both the pivot axis and the rotation axis simultaneously.

Motor 32 includes a rotating shaft 70 which is connected to pivot mechanism 30. Shaft 70 can be attached to pivot mechanism 30 by interference or similar fit, or by other fixed attachment (e.g. by adhesive, solder or welding) within a hole in base 50. Shaft 70 is a hollow shaft (i.e. the shaft has a conduit extending therethrough) and extends through the entirety of motor 32. The conduit through shaft 70 forms a portion of the wire guide passage. In some embodiments, the conduit houses cannula 52 and/or electrical conductors or other structures to pass through shaft 70. The hole in base 50 is sized sufficiently to accommodate both a wire guide and the interface with shaft 70.

In particular embodiments, motor 32 is a microminiature motor suitable for containment within chamber 26 of catheter 22. Examples of such microminiature motors include piezoelectric or electromagnetic motors of a size and configuration suitable for containment within chamber 26 of catheter 22. For example, a particular embodiment of motor 32 is a three-phase, coreless, brushless DC electromagnetic motor, which has few components, small size and minimal complexity. In other examples, a piezoelectric microminiature motor may be used for its advantage of not requiring a gearhead (mechanical transmission) to achieve high torque, and to eliminate problems with torque cables and rotary transformers. A microminiature motor 32 (e.g. electromagnetic or piezoelectric) has a diameter in the range of 0.3 mm to 4 mm and in particular embodiments, for example, approximately 2.0 mm.

Motor 32 may be configured to rotate shaft 70 continuously in a single rotational direction. In such embodiments, pivot mechanism 30 and transducer 28 are rotated around the rotation axis of shaft 70 in that single rotational direction. One or more of the back EMF, the ultrasound signal emitted and/or received by transducer 28, and motor saliency can be used as a feedback mechanism to precisely control the rotational position of motor 32 (and transducer 28 rotated by it) relative to the rest of device 20, ensuring proper registration of images obtained through transducer 28. Registration can be accomplished via methods and structures discussed in U.S. Patent Application Ser. No. 61/713,142 entitled "Feedback/Registration Mechanism for Ultrasound Devices" and WO 2014/059299 entitled "Substantially Acoustically Transparent and Conductive Window," which are incorporated by reference herein in their entirety. Motor 32 may alternatively be configured to run in a reciprocating motion, with shaft 70 switching between rotation in a first rotary direction (e.g. for a predetermined time, arc or number of turns) and rotation in a second, opposite, rotary direction (e.g. for a predetermined time, arc or number of turns). Methods and structures relating to a reciprocating motor are discussed in U.S. Patent Application Ser. No. 61/713,135 and WO 2014/059315, each entitled "Reciprocating Internal Ultrasound Transducer Assembly", which are incorporated by reference herein in their entirety.

Coil 80 is a conductor which is wrapped or coiled multiple times about the rotation axis. In the embodiment of FIG. 1, coil 80 is positioned in the axial direction (relative to the rotation axis) between motor 32 and transducer 28 and adjacent to wall 24 of catheter 22. In some embodiments, coil 80 can be positioned within chamber 26 and positioned adjacent to or abutting the inside surface of wall 24. In other embodiments, coil 80 is positioned adjacent to or abutting the outside surface of wall 24. In other embodiments, coil 80 is integrated into wall 24 of catheter 22. In still other embodiments, coil 80 is positioned about a tubular sheath (not shown) which is positioned within catheter 22 and surrounds at least a portion of pivot mechanism 30. In this way, catheter 22 or a sheath provide structural support for coil 80. In other embodiments, coil 80 can be positioned closer to motor 32 or closer to transducer 28.

Coil 80 has multiple windings (i.e. electrically conductive windings) which are positioned concentric to the rotation axis. Coil 80 has at least one end which is connected to a power source (not shown) as by a conductor leading to or toward the operating end of device 20. In some embodiments, coil 80 has two ends which are connected to the power source by conductors leading to or toward the operating end of device 20. In other embodiments, a single conductor conducts a signal toward the operating end of device 20, and a conductive fluid within chamber 26 provides a second conductive path. The power source can be positioned within or without catheter 22 (e.g., integrated with the console). The power source applies an electric current to coil 80. In this way, coil 80 is positioned such that energizing coil 80 (or application of electric current) creates a magnetic field with poles aligned substantially with the rotation axis.

In the FIG. 1 embodiment, magnetic layer 63 has poles which are symmetrically arranged perpendicularly about the pivot axis. Coil 80 creates a magnetic field with poles aligned with the rotation axis. A magnetic field produced by coil 80 will have a pole (e.g. north) closest to pivot member 57 which attracts the opposite pole (e.g. south) of the magnetic layer and the force of attraction between the two poles applies a torque to pivot member 57. The magnitude of the torque can be varied by altering the magnitude of the current applied to coil 80, and the direction of the torque can be changed by reversing the direction of the current and thus the polarity of the magnetic field produced by coil 80. When the torque is large enough to overcome the spring force of bias members 66, pivot member 57 rotates about the pivot axis from the neutral position. Abutment of connector 62 with cannula 52 (or shaft 70 in some embodiments) halts the motion of pivot member 57 at the end of its pivotal range. As noted, the current applied to coil 80 can be varied in order to control the torque and therefore the angular velocity of pivot member 57. When pivot member 57 is at the end of its pivotal range, the current applied to coil 80 can be reduced or eliminated so that the spring force of bias members 66 overcome the torque of the magnetic fields in order to return pivot member 57 to the neutral position. For example, a current that varies over time can be applied, so that a smooth back-and-forth motion of pivot member 57 is achieved, such as for example a current having a sinusoidal waveform. Alternatively, the current may be reversed to create an opposite magnetic field which creates a torque from the repelling magnetic fields and which works in conjunction with the spring force from bias members 66 to return pivot member 57 to or toward the resting position. In some embodiments, an alternating current can be applied to coil 80 to achieve reciprocating pivotal motion of pivot member 57. Other examples of using a coil to drive motion of a transducer are discussed in U.S. Patent Application Ser. No. 61/748,774 and WO 2014/107323, each entitled "Ultrasound Transducer Direction Control" and U.S. Patent Application Ser. No. 61/758,936 and WO 2014/120923, each entitled "3D Catheter-Based Ultrasound Assembly with Gimbal-Mount Transducer and Single-Coil Drive", which are incorporated by reference herein in their entirety.

In some embodiments, one or more acoustically opaque or attenuating features may be placed within the acoustic window such that the ultrasound field crosses the opaque feature at one or both ends of the pivoting range of transducer 28. Connector 62 may be positioned and/or configured such that transducer 28 stops at a moment when the ultrasound field crosses the acoustically opaque feature. The acoustically opaque feature may be added to or integrated with a catheter 22, examples of which are incorporated by reference above. In some embodiments, the bias members 66 are omitted in which case a feedback sensor is used to determine the pivot angle of transducer 28.

Transducer 28 is electronically connected to an imaging system via signal carriers as noted previously. Bias members 66, if made of conductive material, can be linked to transducer 28 and/or the console or power source to carry electrical signals to and/or from transducer 28. In particular embodiments, bias members 66 provide a conduction path from transducer 28 to conductors positioned along arms 56 (not shown). In some embodiments, alternative to or in conjunction with bias members 66, other signal carriers are positioned to carry a signal from transducer 28 toward the console side of device 20. Other examples of signal carriers include conductors (e.g. wires or cables) along wall 24, through the central conduit of a motor shaft 70, via slip ring connections, and/or via metallic film(s) along wall 24. Examples are discussed and shown in U.S. Patent Application Ser. No. 61/714,275 and WO 2014/062512, each entitled "Internal Transducer Assembly with Slip Ring", which are incorporated by reference herein in their entirety.

A portion of chamber 26 immediately surrounding transducer 28 extending towards the application end of catheter 22 can be completely filled with a coupling fluid or other substance having acoustic impedance similar to that of blood or tissue, such as saline, oils (e.g. mineral oil or castor oil), or mixed alcohol. A seal, bearing, or other structure (not shown for clarity) is positioned adjacent to shaft 70 to provide a fluid seal between motor 32 and the chamber surrounding transducer 28. The substance should minimize friction acting against transducer 28 during rotation.

The coupling fluid and the material of catheter 22 allow acoustic matching to be achieved between body fluids and the medium immediately surrounding transducer 28. Acoustic matching ensures that minimal signal losses occur when transmitting and receiving ultrasound signals between transducer 28 and body tissue which enhances the clarity of the resulting image. The fluid can be added to device 20 during manufacture, or alternatively could be added prior to use. When transducer 28 is sealed and the coupling fluid is placed into the chamber during manufacture, long term contact with the parts necessitates a non-corrosive fluid such as mineral oil or castor oil in order to preserve the shelf life of the product. Preferably, the oil is bio-compatible, acoustically transparent, and has low viscosity. Alternatively, a fluid communication port (not shown) may be positioned or creatable within the catheter or through the catheter wall to allow access for adding a fluid. In that case a corrosive fluid may be added at a time prior to the use of device 20. Corrosive fluids such as water, saline, and alcohol typically have more favorable combinations of bio-compatibility, acoustic transparency, and viscosity.

An example of using device 20 will now be given. Device 20 is prepared (e.g. including injecting a fluid into chamber 26, if not already present), inserted into the body of a patient, and maneuvered to a desired location (e.g. in a particular blood vessel). In some embodiments transducer 28 may be operated during travel to the desired location, such as when transducer 28 has a forward neutral position and can be pivoted through use of coil 80. Throughout placement and at a desired imaging location, motor 32 can be operated to turn transducer 28 around the rotation axis to provide images of tissue(s) or other matter around device 20. Coil 80 can be energized in order to pivot transducer 28 about the pivot axis to shift the ultrasound field forward and/or laterally. Correspondingly, transducer 28 rotates about one or both the rotation axis and the pivot axis. In this way, device 20 provides an ultrasound signal sweep (or field) that not only turns around the rotation axis of device 20, but also around the pivot axis in order to look forward and/or laterally of a particular position of transducer 28. Such two-axis movement is capable of providing 3D images, although device 20 could also be rotated about a single axis to provide 2D images (an additional embodiment configured solely for 2D imaging is described herein below, with reference to FIG. 13).

When an ultrasound signal is transmitted, the ultrasound signal passes across wall 24 of catheter 22 until it encounters an acoustic impedance boundary or strong scattering source (e.g. body tissue, plaque, medical implant, or other material which has acoustic impedance sufficiently different from bodily fluids or other surrounding material) such that the ultrasound signal is at least partially reflected at the boundary. At least a portion of the ultrasound signal is reflected back or scattered towards transducer 28. One or more electrical signals representing reflected ultrasound received at transducer 28 are sent from transducer 28 via a conduction pathway to the ultrasound console, for imaging and/or other data display to the physician. Simultaneously or subsequently transducer 28 continues to emit further ultrasound signals and the process is repeated continuously in certain embodiments and over a desired period of time.

Figure 3:
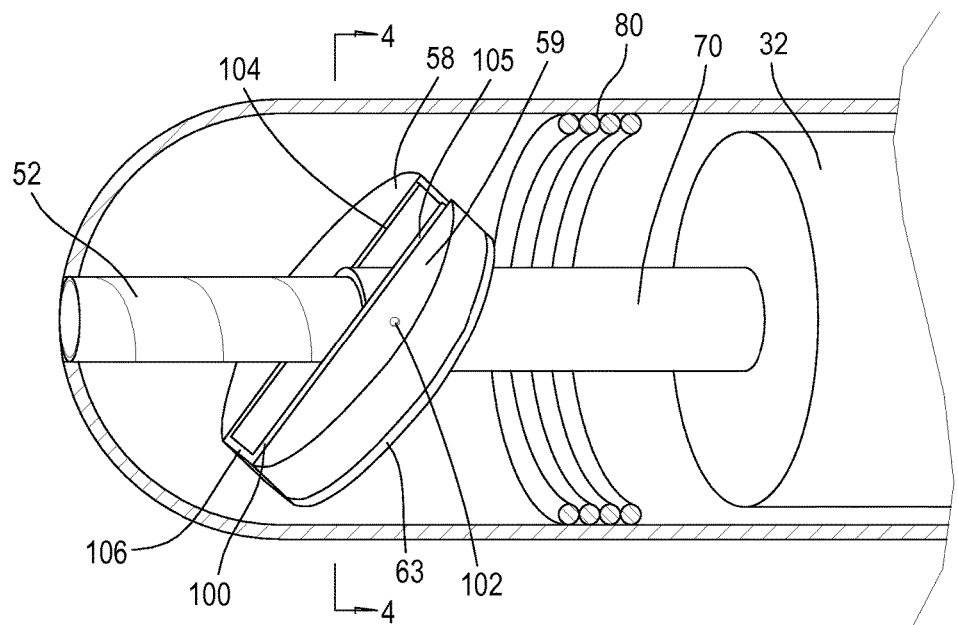
FIG. 3 is an illustrative perspective view of an embodiment of a 3D imaging ultrasound device having a split transducer attached to a motor shaft.

An alternative embodiment of device 20 configured for 3D imaging is shown in FIG. 3. The embodiment of FIG. 3 is the same in structure and function as that already described, with the exception of the differences discussed herein. A feature of the FIG. 3 embodiment is that instead of a gimbal-type pivot mechanism having arms 56, pivot member 57 is rotatably mounted directly to shaft 70. Shaft 70 extends at least to the pivot axis of pivot member 57, and at least a portion thereof extends between sections 58, 59. Pivot member 57 includes a u-shaped mounting piece 100 positioned between sections 58, 59. A rotatable coupling 102 allows pivot member 57 to rotate relative to shaft 70.

Mounting piece 100 has two legs 104, 105. A support 106 extends between and connects legs 104, 105. Mounting piece 100 is a rigid structure that provides structural support for sections 58 and 59. Mounting piece 100 can be a single part or it can be formed by connecting support 106 to legs 104, 105. Sections 58, 59 are attached to mounting piece 100 so that mounting piece 100 rotates in unison with sections 58, 59. Mounting piece 100 as illustrated in FIG. 3 has a thickness that is generally the same as the thickness of the pivot member 57 to provide increased surface area for attachment to and support of sections 58, 59. In other embodiments, the thickness of mounting piece 100 is less than the thickness of sections 58, 59.

Figure 4:
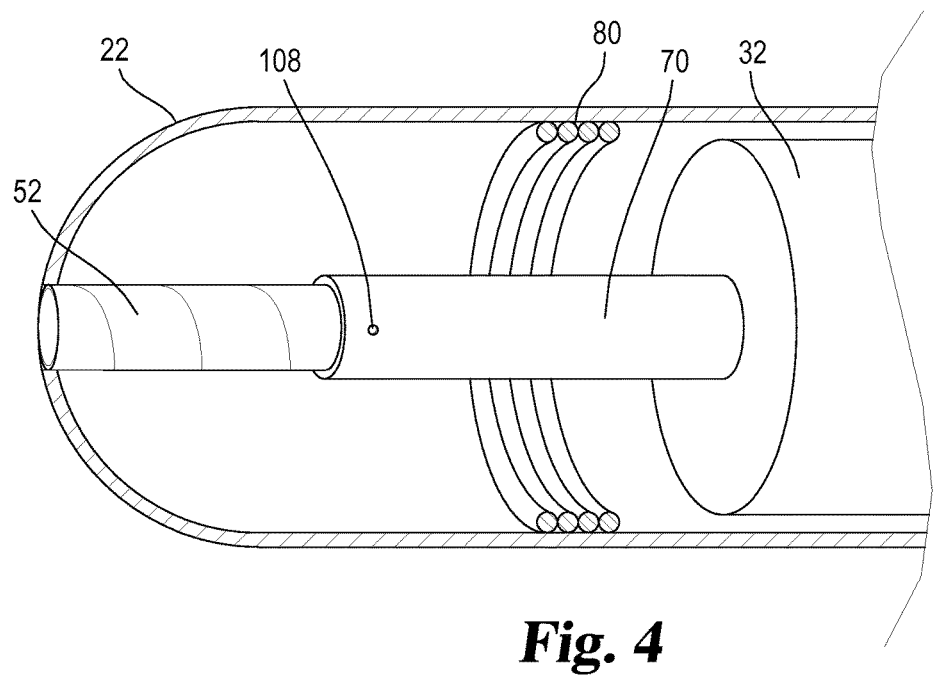
FIG. 4 is a partial perspective view of an embodiment of the ultrasound device of FIG. 3 with the split transducer removed.
Figure 5:
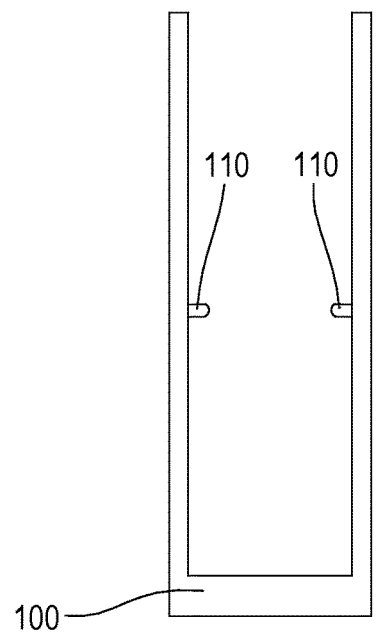
FIG. 5 is a front view of a mounting piece and pivot rods for supporting the transducer of FIG. 3.

Coupling 102 can be formed in a variety of different ways in various embodiments. In one embodiment, coupling 102 includes depressions 108 and pivot rods 110. A pair of depressions 108 positioned on the outer surface of shaft 70 serve as pivot points (e.g. FIG. 4). Pivot rods 110 are sized to fit into and interact with the depressions 108 so that each pairing of a pivot rod 110 and a depression 108 creates a joint that allows pivot rod 110 to rotate within depression 108. Depressions 108 are positioned opposite from one another along the pivot axis. Depressions 108 are generally hemispherical depressions in the surface of shaft 70, although other shapes are suitable, such as a conical shape with a rounded bottom, for example. Mounting piece 100 has pivot rods 110 that extend from the inward surface of legs 104, 105 along the rotation axis. Pivot rods 110 can be constructed with a rounded end (FIG. 5), a pointed end, a flat end, or a variety of other structures that are suitable to create a pivot joint when paired with depressions 108. During construction, mounting piece 100 can be attached to shaft 70 by moving frame 100 over shaft 70, aligning pivot rods 110 with depressions 108, and allowing pivot rods 110 to snap or move into depressions 108. Generally, mounting piece 100 includes sufficient elastic properties to cause pivot rods 110 to engage with depressions 108 so that pivot member 57 is secured to shaft 70. The shapes of pivot rods 110 and depressions 108 cause minimal friction which allows pivot member 57 to pivot substantially freely about the pivot axis. Other embodiments include variations of the positioning and arrangement of depressions 108 and pivot rods 110. As one example, depressions 108 are positioned on the inner surfaces of legs 104 and 105 and pivot rods 110 are positioned on shaft 70.

Figure 6:
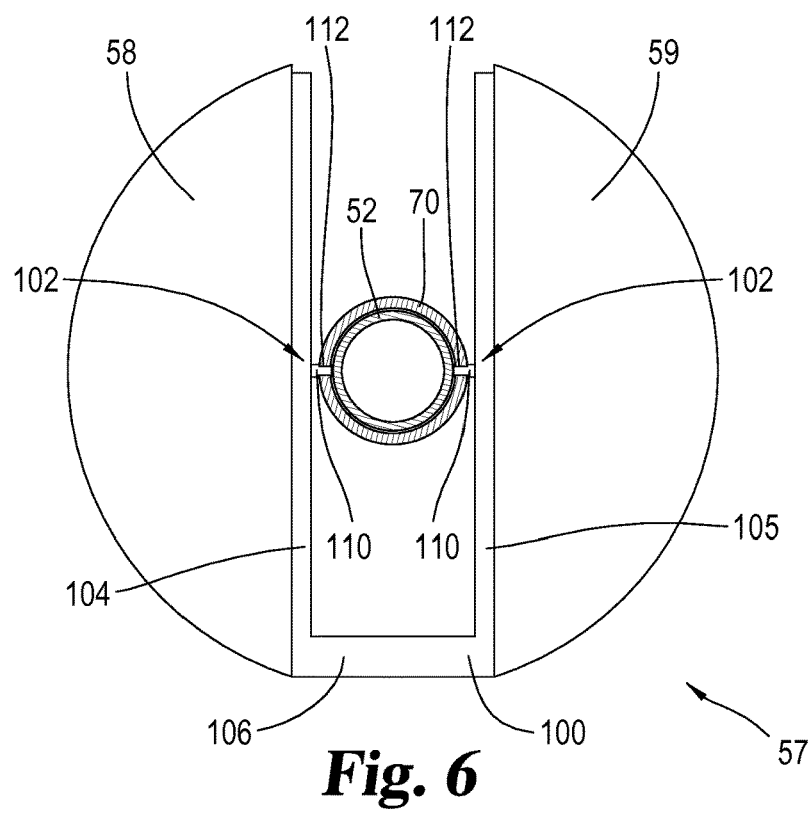
FIG. 6 is a partial cross-sectional front view of an end of an embodiment of the ultrasound device of FIG. 3.
Figure 7:
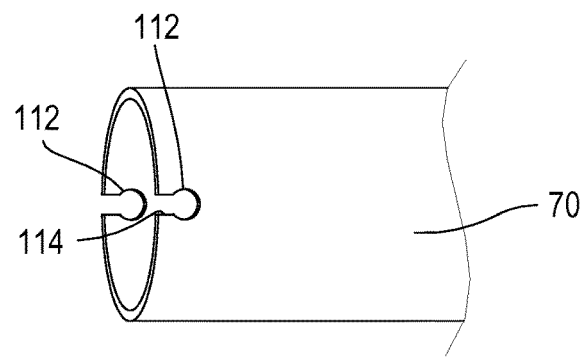
FIG. 7 is a partial perspective view of an alternative motor shaft embodiment of the ultrasound device of FIG. 3.
Figure 8:
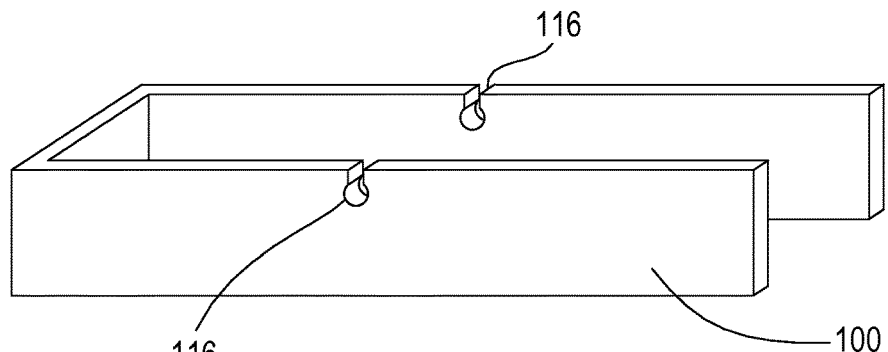
FIG. 8 is a partial perspective view of an alternative mounting piece embodiment of the ultrasound device of FIG. 3.

In other embodiments, coupling 102 includes notches configured to interact with pivot rods 110. An example of a coupling 102 having pivot rods 110 positioned on mounting piece 100 and notches in shaft 70 is shown in FIG. 6. FIG. 7 shows shaft 70 having notches 112 positioned at the end of shaft 70. Notches 112 are positioned along the pivot axis and are configured to accept pivot rods 110 which are sized and shaped to be insertable into notches 112. In the illustrated embodiment, notches 112 are shaped with a circular bearing surface that is accessed by a narrow insertion channel 114. The channel 114 allows pivot rods 110 which are slightly wider than channel 114 to be inserted through channel 114 and secured into notches 112 through an elastic property of the material containing the notches 112. In other embodiments, notches 112 are shaped differently. Other embodiments of coupling 102 include variations of the positioning and arrangement of notches 112 and pivot rods 110. As an example, FIG. 8 shows mounting piece 100 having notches 116 positioned in each leg 104, 105 along the pivot axis. In that embodiment, pivot rods positioned along the pivot axis on shaft 70 (not shown) are configured to snap into notches 116.

Figure 9:
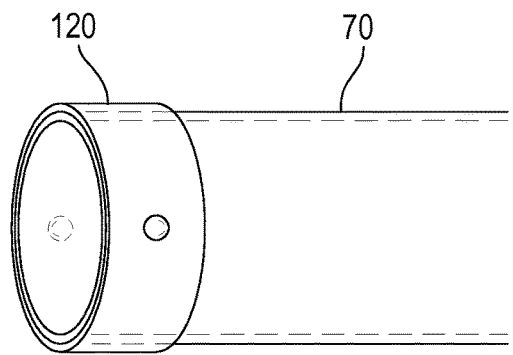
FIG. 9 is a partial perspective view of an alternative embodiment of the end of the motor shaft having a collar.

Other embodiments include a collar 120 placed on the end of motor shaft 70 (FIG. 9). The collar includes part of coupling 102. For example, in some embodiments, the collar includes depressions or notches as previously described that are configured to interact with pivot rods 110 on mounting piece 100. In other embodiments, the collar includes pivot rods 110 which are configured to interact with depressions or notches positioned on mounting piece 100 as previously described.

Coupling 102 can include a portion of the conduction path between transducer 28 and the control end of device 20. In embodiments having pivot rods and depressions, the pivot rods and depressions can be constructed of or plated with a conductive material. Similarly, in embodiments having pivot rods and notches, the pivot rods and notches can be constructed of or plated with a conductive material. Wire leads (not shown) extending both from transducer 28 and from the control side end of device 20 are connected to the depressions (or notches) and pivot rods. The physical connection between the depressions (or notches) and the pivot rods provide passage of electric signals between the wire leads. In some embodiments, the pivot rods and depressions (or notches) are constructed as separate conductive pieces integrated into shaft 70 and mounting piece 100. In other embodiments, a conductive coating or plating material can be applied to the pivot rods and depressions (or notches). In any case, the conductive portions are constructed appropriately (or sufficient insulation is provided) to avoid a short-circuit between the wire leads. In still further embodiments, wire leads connected to transducer 28 extend separately along shaft 70 towards the control end of device 20. In that case, the wire leads can extend along the outside surface and/or the inside surface of shaft 70.

Figure 10:
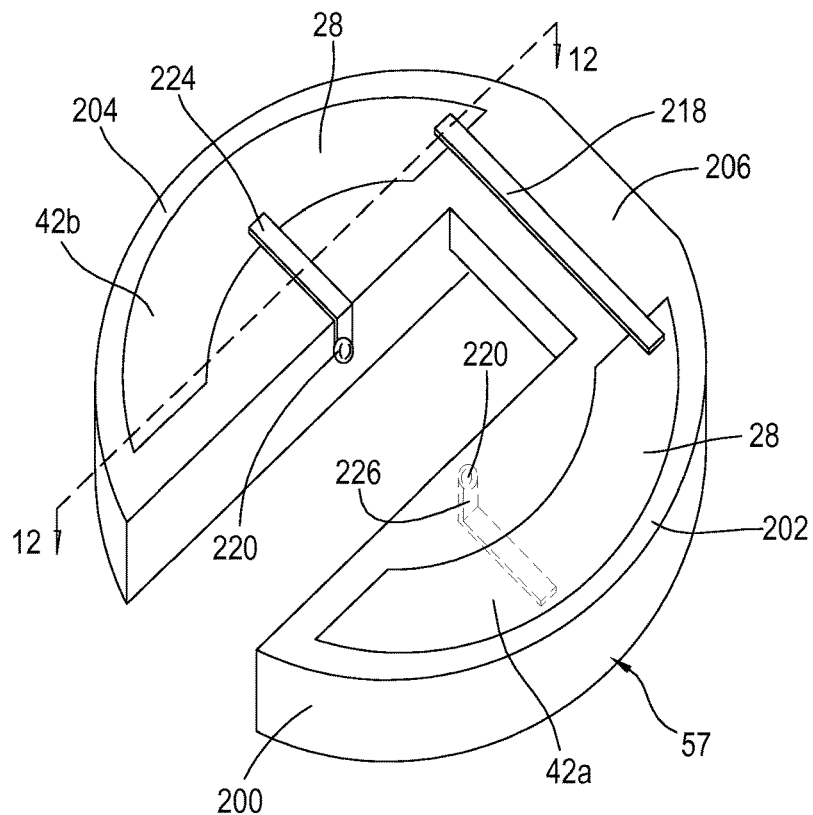
FIG. 10 is a partial perspective view of an alternative embodiment of the pivot member.
Figure 11:
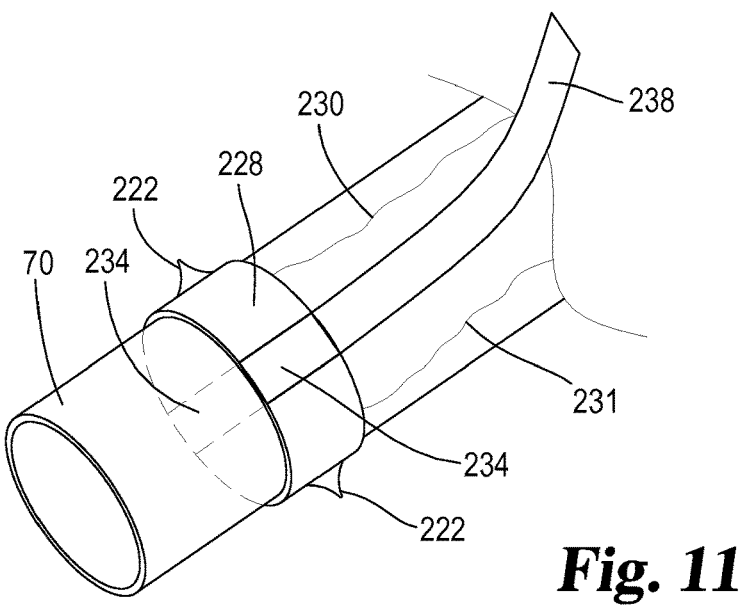
FIG. 11 is a partial perspective view of an alternative embodiment of the motor shaft.
Figure 12:
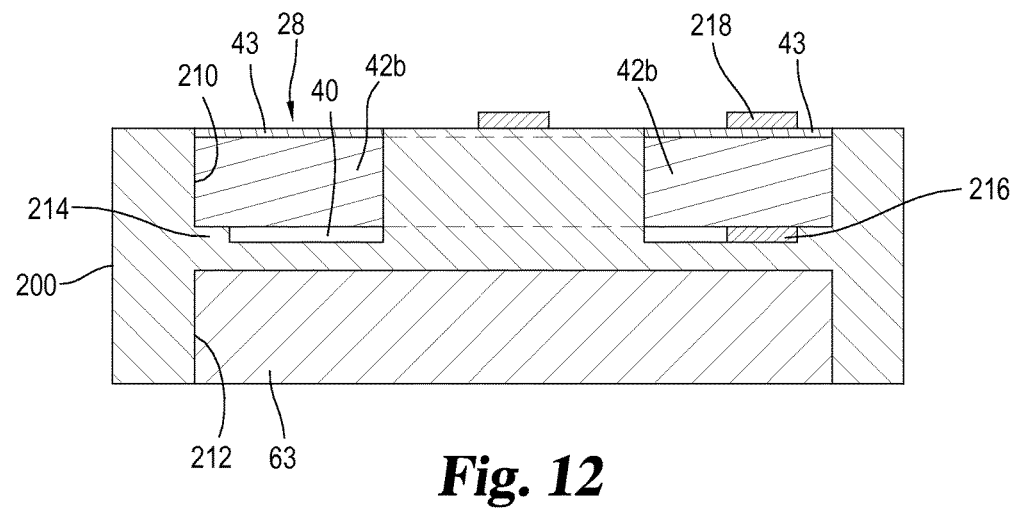
FIG. 12 is a side cross-sectional view of the pivot member of FIG. 10.

An alternative embodiment of device 20 configured for 3D imaging is shown in FIGS. 10, 11, and 12. The embodiment of FIGS. 10, 11, and 12 is the same in structure and function as already described for the other embodiments with the exception of the differences discussed herein with respect to FIGS. 10, 11, and 12. In this embodiment, pivot mechanism 30 includes pivot member 57 having a structure 200 that is a molded piece mountable to shaft 70. Structure 200 provides support for transducer 28 and includes a pair of pivot connectors, magnet layer 63, and wiring for transducer 28.

Structure 200 is generally injection molded from a rigid polymer. Structure 200 includes sections 202, 204 and a connector portion 206. Each section 202, 204 has an upper portion with a cavity 210 that is configured to house a portion of transducer 28 and a lower portion with a cavity 212 that is configured to house magnetic layer 63. Cavities 210, 212 are shown in FIG. 12 which depicts a cross section of a portion of pivot member 57.

Cavities 210 are crescent shaped in the present embodiment. Similarly, transducer 28 is split, and each split portion is crescent shaped. The crescent shaped portions of transducer 28 can provide enhanced focusing and imaging when transducer 28 is placed over shaft 70. The enhanced focusing and imaging occurs by providing a distance between the split portions of transducer 28 and shaft 70, so that shaft 70 interferes minimally or not at all with an ultrasound signal emitted received from transducer 28. In other embodiments, cavities 210 can be shaped as partial circles rather than crescent shaped.

Cavities 210 include one or more shoulders 214 positioned at the base of the cavity and at one end of the crescent shaped cavities 210. A conductor 216 extends between the bases of cavities 210 and through connector portion 206. An ultrasound element 42 is positioned within each of the cavities 210. Matching layers 43 are positioned adjacent to each of the top surfaces of elements 42. For clarity, element 42 positioned in cavity 210 of section 202 is also referenced as element 42a and element 42 positioned in cavity 210 of section 204 is also referenced as 42b.

Elements 42a and 42b abut against shoulder 214 and conductor 216 so that elements 42 are suspended from the bottom surface of cavities 210 to create air layers that serve as backing 40 in this embodiment. The edges of elements 42a, 42b are sealed to the sides of cavities 210 with glue (although other methods of attachment could be used, such as friction fit) so that fluids cannot enter cavities 210 and compromise the air layers. In other embodiments, multiple shoulders 214 are positioned within cavities 210, and in some embodiments shoulder 214 can be used in place of conductor 216 to help create backing 40 as a layer of air. In other embodiments, backing 40 can be a layer of material positioned at each base of cavities 210, in which case shoulders 214 can be omitted. In still further embodiments, elements 42 can include an array of smaller rectangular-shaped elements that are oriented to fit within cavities 210.

Cavities 212 are configured to hold magnetic layer 63, which can be included as a two-part layer with one part in section 202 and the other part in section 204. Magnetic layer 63 can be formed in two parts as partial circular shapes or as crescent shapes in each section 202, 204. In other embodiments, the magnet layer 63 is included in only one of sections 202, 204.

The pivot connectors rotatably connect pivot member 57 to shaft 70. Indentations 220 are positioned in structure 200 and serve as bearing surfaces that mate with a pair of protrusions 222 attached to shaft 70. The two indentations 220 are positioned along the pivot axis on the inside surfaces of sections 202, 204 and can be constructed as dimples or depressions in the surface of structure 200. Alternatively, indentations 220 can be constructed as molded features protruding from the surface of structure 200. Protrusions 222 are attached to or are a part of sleeve 228 that is attached to shaft 70. In other embodiments, protrusions 222 are attached to or are a part of shaft 70. Protrusions 222 are generally conical shaped or shaped as a shaft with a pointed or rounded end. Protrusions 222 are positioned along the pivot axis and are configured to interact with indentations 220 and provide a rotatable connection between shaft 70 and pivot member 57. The contact between protrusions 222 and indentations 220 acts as a bearing surface to allow pivot member 57 to rotate relative to shaft 70 about the pivot axis.

Various conductors are included to electrically connect elements 42a and 42b while also allowing passage of signals between pivot member 57 and shaft 70. A conductor 218 is positioned on a top surface of structure 200 and extends between elements 42a and 42b. In some embodiments, conductor 218 pierces the matching layers 43 to make contact with elements 42a and 42b. In other embodiments, the matching layers 43 are electrically conductive and provide an electrical connection between conductor 218 and elements 42a, 42b. In any case, conductor 218 electrically connects the top surface of element 42a to the top surface of element 42b. Similarly, conductor 216 electrically connects the bottom surface of element 42a to the bottom surface of element 42b. In that way, elements 42a, 42b can function as a single transducer by providing that the two elements 42a, 42b are electrically common and can simultaneously transmit and receive a single ultrasound signal.

In the illustrated embodiment, the pivot connectors are configured to pass electrical signals between transducer 28 and conductors 230, 231 extending along shaft 70. Conductors 224, 226 are electrically connected to one each of indentations 220. Conductor 224 is electrically coupled with the top surface of element 42b. Conductor 226 is electrically coupled with the bottom surface of element 42a. Conductor 226 is configured to pass through the wall of structure 200 to gain access to the bottom surface of element 42 in section 202. In some embodiments, conductors 216, 218, 224, and 226 are molded into structure 200 during manufacture. Indentations 220 can be constructed of a conductive material or plated with a conductive material to form an electrical contact with conductors 224, 226. Similarly, in some embodiments, protrusions 222 can be constructed of a conductive material or plated with a conductive material to form an electrical contact with sleeve 228. Sleeve 228 can be constructed of a conductive material in which case sleeve 228 includes insulator portions 234 which electrically isolate protrusions 222 from one another. Sleeve 228 is similarly insulated from shaft 70 if shaft 70 is constructed of a conductive material. Conductors 230, 231 are connected to sleeve 228.

In other embodiments, sleeve 228 is constructed of a non-conductive material, in which case conductors 230, 231 are connected directly to protrusions 222 (not shown). Conductors 230, 231 are wires or other suitable conductors that extend along shaft 70 and couple with a slip ring assembly or other suitable mechanism for passing electric signals between the control side of motor 32 and transducer 28. In other embodiments, the pivot connectors are not configured to pass electrical signals in which case flexible wires extend directly from transducer 28 to couple with the slip ring or other suitable mechanism.

A leaf spring 238 is attached to shaft 70 either directly or through sleeve 228 in the illustrated embodiment. Leaf spring 238 provides a return force for pivot member 57, and tends to push the imaging surfaces of transducer 28 toward the application end of catheter 22 (or toward the forward facing orientation). Leaf spring 238 is attached to shaft 70 so that it engages connector portion 206 of pivot member 57. The magnetic force between coil 80 and magnet layer 63 opposes the spring force of leaf spring 238. As described previously, control of the current through coil 80 provides control of the movement of pivot member 57 about the pivot axis.

Further alternative embodiments of the imaging devices having two axis motion as described herein include variations of pivot mechanism 30 and the magnetic layer. In one embodiment, the magnetic layer is a permanent magnet having poles aligned along an axis which is normal to the major surfaces of sections 58, 59 (or sections 202, 204). In this embodiment, a magnetic field produced by coil 80 has a pole closest to the magnetic layer which repels the pole of the magnetic layer closest to coil 80. When coil 80 is energized, a repellant force creates a torque on pivot member 57 which causes it to rotate about the pivot axis. In other embodiments, the magnetic layer is isolated to a portion of one or both of sections 58, 59 (or sections 202, 204) in which the polls are aligned along an axis which is normal to the major surface of the disc. In other embodiments, one of sections 58 or 59 (or one of sections 202 or 204) is constructed as the transducer 28 and the other section 59 or 58 comprises the magnet layer. In other embodiments, bias members 66 bias pivot member 57 to other (non-forward-facing) neutral positions. In one example, in the neutral position the viewing angle of transducer 28 is perpendicular to the rotation axis, and a repulsion force from the magnetic fields causes pivot member 57 to rotate about the pivot axis toward the forward facing position (i.e. with transducer 28 viewing angle aligned with the rotation axis).

Controls for motor 32 and/or coil 80 may be provided to maintain rotational motion of transducer 28 about the rotation axis and pivot axis at a particular rotational speed or pattern. For example, modalities such as a spin around the rotation axis of between 30-100 Hz may be combined with a slower pivoting around the pivot axis of about 1-2 Hz, to provide clear images forward and backward in a defined pattern. It has also been determined that a relatively slow spin around the rotation axis (e.g. about 1-2 Hz) combined with pivoting around the pivot axis more rapidly, e.g. near a resonant frequency of device 20 can provide good results. A modality providing a faster rotation around the rotation axis when transducer 28 is pointed closer to the rotation axis and slower rotation around the rotation axis when transducer 28 is further from the rotation axis is also useful for improving the image frame rate and clarity. Imaging continues, with adjustments to the positioning of transducer 28 and the ultrasound field, as the physician deems necessary or useful.

An additional embodiment is described herein with reference to FIG. 13, which shows a portion of an exemplary device 20 configured for 2D imaging, having a transducer 28 that rotates about a single rotation axis A. Device 20 includes catheter 22, cannula 52, motor 32, shaft 70, and transducer 28 as described herein. Transducer 28 is attached to a surface of shaft 70 so that it is offset from the rotation axis A. In the illustrated example, transducer 28 is a single element transducer. Transducer 28 is rotatable through a path (or rotation path) over cannula 52 about the rotation axis and is configured so that it fits in the space between wall 24 and shaft 70. Shaft 70 accommodates cannula 52, which forms all or a portion of the wire guide passageway.

In the illustrated embodiment (FIG. 13), a slip ring assembly 90 is attached or positioned adjacent to motor 32 and shaft 70 and provides an electrical connection between rotating conductors 92 and non-rotating conductors 94. Non-rotating conductors 94 are routed through the catheter in the control direction to connect to the console (not pictured). In one embodiment, non-rotating conductors 94 are routed along the inside surface of wall 24. Rotating conductors 92 are connected to transducer 28. Descriptions of slip ring configurations are incorporated herein above. In other embodiments, motor 32 is configured to reciprocate, descriptions of which are incorporated herein above.

Figure 14:
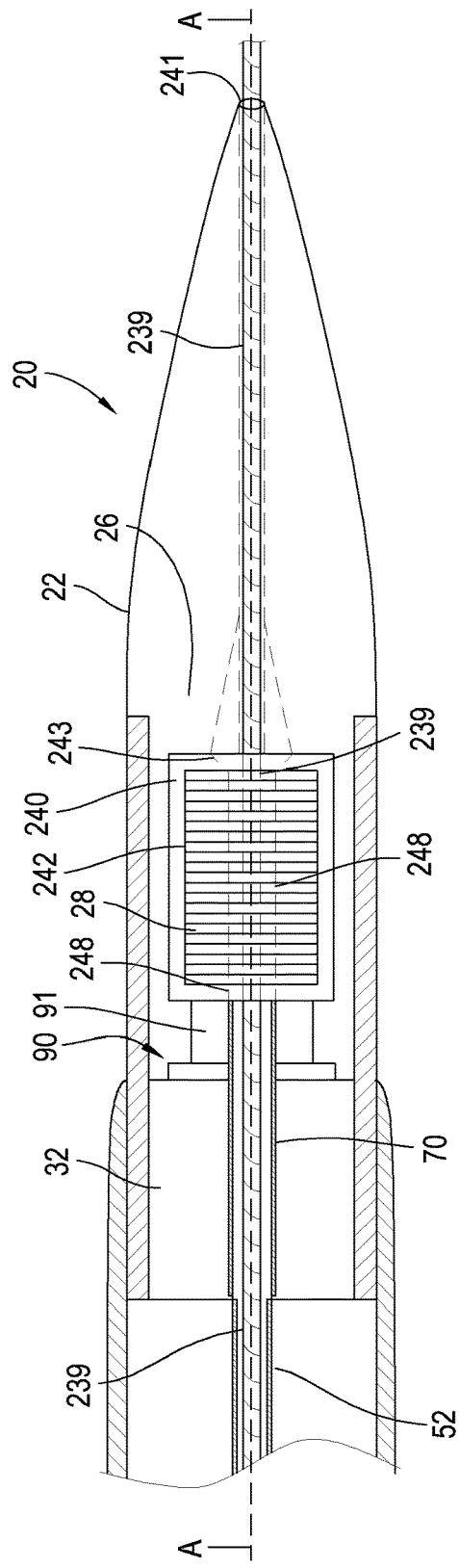
FIG. 14 is an illustrative top view of an alternative embodiment of the ultrasound device having a rotating linear array transducer and a mounting piece.
Figure 15:
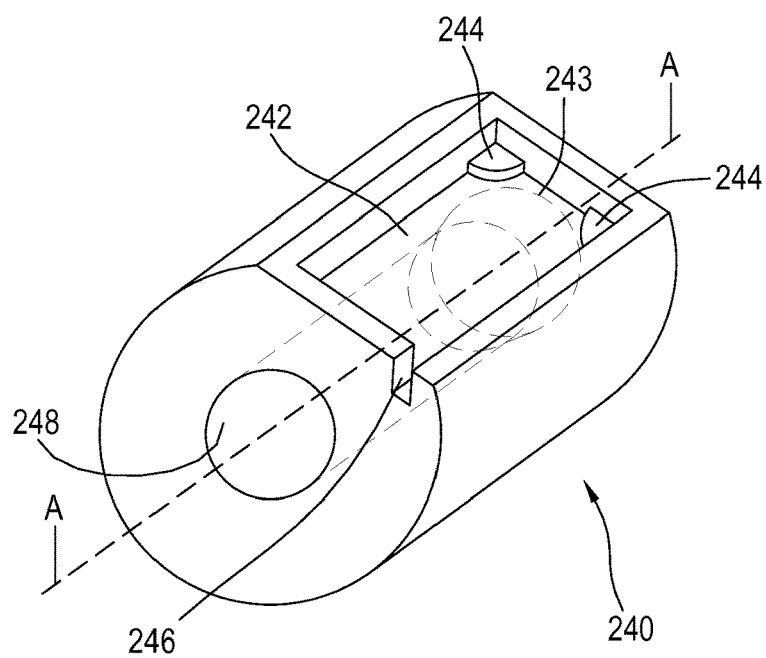
FIG. 15 is an illustrative perspective view of an alternative embodiment of the transducer mounting piece of FIG. 14.
Figure 16:
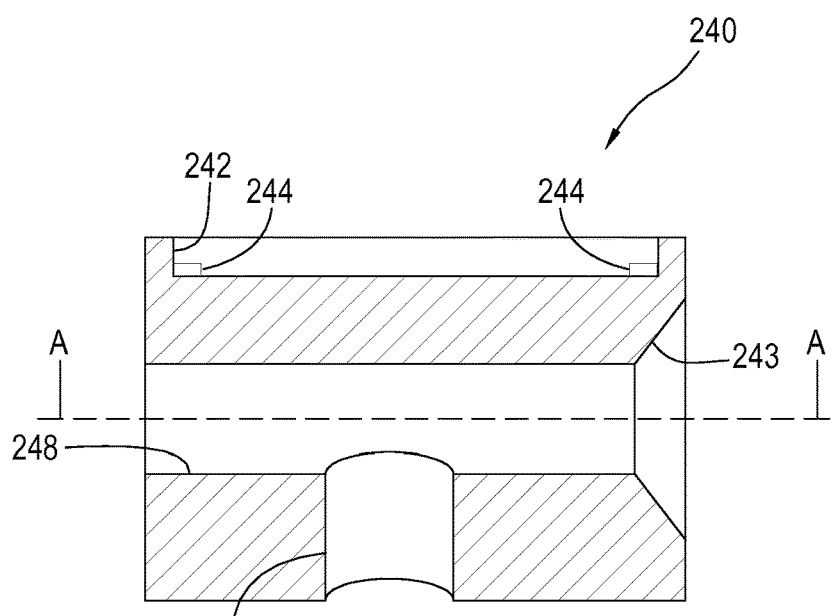
FIG. 16 is an illustrative side view of the mounting piece of FIG. 15.

An additional embodiment is described herein with reference to FIGS. 14, 15, and 16, which shows a portion of an exemplary device 20 configured for 3D imaging. Device 20 has a transducer 28 configured as a linear array transducer that rotates about a single axis and about the wire guide channel. In that embodiment, device 20 includes catheter 22, cannula 52, motor 32, shaft 70, transducer 28, slip ring assembly 90, and mounting piece 240. In the illustrated example, transducer 28 is a linear array transducer. Such linear array transducers are capable of providing three-dimensional imaging while rotating about a single axis. The wire guide channel extends through cannula 52, shaft 70, mounting piece 240, and the application end of catheter 22. An exemplary and removable wire guide 239 is shown in FIG. 14. Cannula 52 extends and attaches to the control side of motor 32.

Although the embodiment shown in FIG. 14 includes a linear array transducer, mounting piece 240 can be configured to house either a single element transducer or a linear array transducer. An embodiment of mounting piece 240 configured to house a single element transducer is shown in FIG. 15. Mounting piece 240 includes cavity 242 which houses transducer 28, including backing 40, ultrasound elements 42, and matching layer 43 (not shown in FIG. 15). In embodiments of mounting piece 240 configured to house a single element transducer, cavity 242 can include shoulders 244 positioned at corners of cavity 242 to suspend transducer element 42 above the bottom surface of cavity 242 thereby creating a space for a backing layer having low acoustic impedance compared to elements 42.

Electrical connections between the rotatable transducer 28 and relatively stationary catheter are made through use of slip ring assembly 90 that is sandwiched between mounting piece 240 and motor 32. In one embodiment, the rotating portion of the slip ring assembly 91 is glued or otherwise attached to the surface of the mounting piece 240 that faces the motor. In another embodiment, the rotating portion of the slip ring assembly 91 is insert-molded into the mounting piece. A notch 246 allows passage of a conductor between the bottom surface of transducer 28 and the slip ring assembly 90.

A bore 248 extends along or substantially parallel to the rotation axis A through mounting piece 240 and provides attachment to shaft 70 as well as defining a portion of the wire guide channel. In some embodiments, bore 248 includes one or more side passageways 249 that extend generally radially relative to the rotation axis A that serve as fluid injection ports (FIG. 16). Examples of such structures for fluid injection are explained in U.S. Patent Application Ser. No. 61/885,149, entitled "Over-the-Wire Ultrasound System with Dual-Purpose Channel for Wire guide and Fluid Injection", and incorporated herein by reference in its entirety. Side passageway(s) 249 are configured to allow injection of a coupling fluid (e.g. saline, oils, or alcohols) into chamber 26 to give chamber 26 ultrasound characteristics similar or substantially identical to that of the wall of catheter 22 and the surrounding bodily environment (e.g. the blood stream). By including side passageway(s) 249 into a mounting piece 240, the wire guide passageway can provide both a passage for the wire guide as well as a path for injecting a coupling fluid.

Bore hole 248 through mounting piece 240 preferably has a slightly larger diameter than the inner diameter of cannula 52 and a passageway through the application end of catheter 22. Bore hole 248 includes a taper 243 at the application end so that when inserting a wire guide through a lumen 241 at the application side tip of catheter 22, the wire guide will easily slip into bore 248 when inserted into taper 243. Lumen 241 is molded into a portion of the application side tip of catheter 22 and extends from the application end of catheter 22 through at least a portion of the tip of catheter 22 without intruding upon chamber 26. The larger diameter of bore 248 and the inner surface of shaft 70 compared to cannula 52 and lumen 241 allow the rotatable parts of device 20 (i.e. mounting piece 240, shaft 70, etc.) to rotate without excessive interference or rubbing from wire guide 239 which is partially constrained in the radial direction relative to axis A by the narrower lumen 241 and cannula 52.

In some embodiments, mounting piece 240 is configured to house an array of elements 42 as shown in FIG. 14. In that case, shoulders 244 are replaced with a structure that extends along two walls of cavity 242 to provide support for each element 42. Alternatively, backing 40 can include a layer of material that provides support for one or more elements 42. In some embodiments, mounting piece 240 itself serves as backing 40 of transducer 28.

In various embodiments, mounting piece 240 and transducer 28 can be configured to provide alternate orientations of transducer 28. In the illustrated embodiments of FIGS. 14, 15, and 16, transducer 28 is configured as a single element transducer or a linear array transducer with a surface that is substantially flat. In other embodiments (not shown), cavity 242 can be configured to house transducer 28 so that it has a surface that is nonparallel relative to the rotation axis A. In one exemplary embodiment, cavity 242 has a bottom surface that is angled so that the face of transducer 28 is angled towards the application side end (or tip) of catheter 22 to provide more forward facing three-dimensional imaging capabilities. In other embodiments, mounting piece 240 and cavity 242 can be configured to provide any of a variety of desired shapes, such as curved or concave, for example. In such case, the bottom surface of cavity 242 can be configured as a concave or curved surface (for example) so that one or more elements 42 positioned within cavity 242 create a surface of transducer 28 that is curved or concave. In other embodiments, an acoustic lens is added to matching layer 43 as described previously.

In some embodiments including a linear array transducer, beamforming circuitry (not shown) is included in mounting piece 240. Separate circuits can be included for both transmitting and receiving an ultrasound signal. The beamforming circuitry for the transmitting signal can include a demultiplexer along with other circuit components that activate specified elements of transducer 28 according to the particular configuration of transducer 28. The circuitry for the receiving signal can include a multiplexer to convert the multiple signal lines from the multiple elements 42 to one signal line. Placing circuitry on or in a rotating part of device 10 (e.g. mounted within mounting piece 240 or transducer 28) allows for simplification of the cabling and design of slip ring assembly 90. One signal line can run from the control end of catheter 22 and through slip ring assembly 90. This feature makes it possible to incorporate a linear array transducer assembly into a rotating design.

In some embodiments of device 20, a portion of mounting piece 240 that abuts against slip ring assembly 90 can be coated with a hydrophobic coating or constructed with a hydrophobic surface so that the coupling fluid does not enter the section of chamber 26 between mounting piece 240 and the motor 32, which contains slip ring assembly 90. The hydrophobic coating helps to ensure that the section of chamber 26 around slip ring assembly 90 contains air and/or a non-conductive lubricant (e.g. grease, silicon oil, mineral oil, or other oils) rather than coupling fluid.

During use, mounting piece 240 provides the ability to combine both the wire guide channel and a fluid injection port with an over the wire linear array transducer design. Coupling fluid is injected from the handle of catheter 22 (typically using a syringe) prior to insertion of catheter 22 into a body. The coupling fluid passes through side passageway(s) 249 of mounting piece 240 and enters chamber 26. The coupling fluid may be injected while the transducer is spinning to promote passage of the water through the side passageway. The coupling fluid flushes air from within chamber 26 surrounding transducer 28. The hydrophobic surface or coating located at the control side of mounting piece 240 and/or slip ring assembly 90 repels the coupling fluid and prevents it from entering the portion of chamber 26 containing slip ring assembly 90 and the beamforming circuitry.

Figure 17:
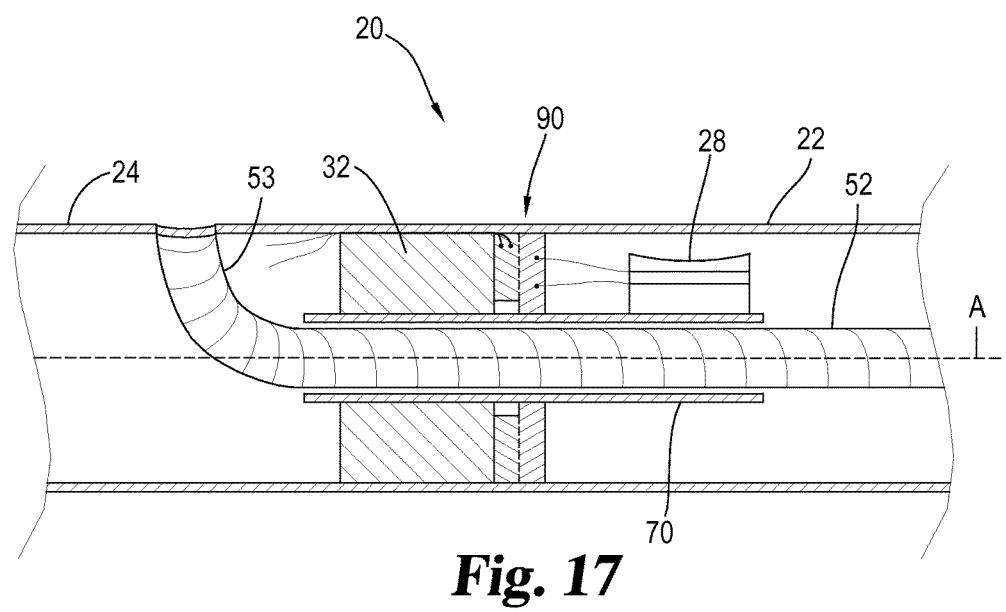
FIG. 17 is an illustrative side view of an alternative embodiment of the ultrasound device configured for use in a rapid exchange system.

The embodiments of device 20 described herein can be configured for use in a rapid exchange system. An exemplary embodiment is shown in FIG. 17. In that embodiment, cannula 52 has a portion 53 that extends through wall 24 of catheter 22 on the control side of motor 32. Such a configuration allows a wire guide or coupling fluid to be inserted near the tip of catheter 22 near the control side of motor 32. In that embodiment, cannula 52 and/or the wire guide passageway is configured to run along or substantially parallel to the rotation axis A for at least the portion of device 20 that includes motor 32 and transducer 28. In other words, transducer 28 is rotatable about a wire guide passageway extending through the tip of catheter 22 even when the wire guide passageway is configured for use in a rapid exchange system.

The embodiments of device 20 described herein facilitate capture of an image through an acoustic window which is free from unnecessary acoustic attenuation such as artifacts, obstructions, or errors. For example, positioning of transducer 28 at a location which is on an application side of motor 32 ensures that parts of device 20 which would create artifacts in a signal (e.g. wires or other echogenic materials) are not positioned within or across the acoustic window of transducer 28, even as transducer 28 rotates in a full 360° rotation about the rotation axis as well as pivoting about the pivot axis. In this way, there are no wires or other reflecting materials which could cause artifacts within the image or block portions of the redirected ultrasound waves. This provides the physician a clear view through the entirety of the acoustic window. As used herein, the term "acoustic window" includes a substantially obstruction-free pathway throughout the structure of device 20 between transducer 28 and organic fluids or tissue which may be positioned external to device 20 during use. In other words, the entire acoustic window has low acoustic attenuation and/or has acoustic impedance that substantially matches blood or water.

Device 20 can be coupled with wire guides which have portions that are capable of exhibiting altered ultrasound characteristics. For example, wire guides having tips which can be altered between an echogenic state and a comparatively echolucent state are discussed and shown in U.S. Application Ser. No. 61/773,199 and PCT/US2014/020374, each entitled "Echolucent Guidewire Tip", which are incorporated by reference herein in their entirety. Pairing of such wire guides with the devices 20 as described herein can be advantageous. In one exemplary configuration, a wire guide having a tip configured to be echolucent when used with the embodiment of FIG. 1 can reduce or eliminate the occurrence of artifacts in the acoustic window.

Device 20 is configured to be used with existing medical devices which are designed for percutaneous, intraluminal, or interstitial procedures. For example, device 20 can be used as or with a variety of catheters for different purposes, e.g. positioned on or within an application side of a catheter, depending on the particular configuration. The particular uses described herein are not indicative of any limiting aspects of the usage capabilities of the device 20.

In some embodiments described herein, hall sensors (not shown), optical encoders (not shown), ultrasound, back EMF, motor saliency, or a combination of one or more of these may be used to control and/or monitor angular positions of motor 32. It has been determined that hall sensors are advantageous as a feedback mechanism because of their small size and mature design. In some embodiments, the ultrasound beam or signals emitted and/or received by transducer 28 is used as a feedback mechanism to precisely assess or monitor the rotational position of motor 32 (and the ultrasound beam rotated by it) relative to the rest of device 20, ensuring proper registration of images obtained through transducer 28. Other features may be included with the embodiments noted herein such as indexing systems.

While some of the above discussion concerned specific use in the context of ultrasound system applications, it will be understood that embodiments of device 20 could also be used for a variety of other medical procedures and with a variety of other medical devices. The versatility of the embodiments described herein allows device 20 to be used to guide percutaneous therapeutic interventions such as, for example, embolism coils, stents, filters, graphs, balloons, biopsies, and administering therapeutics, etc. Device 20 can be used to locate various anatomical landmarks that will be used to correctly place or guide therapy. Typical landmarks include confluences, bifurcations, side-branches, nearby vessels, nearby nerves, the heart, and other tissues adjacent to vessels or other orifices containing the transducer. Device 20 can also be used to locate diseased tissue that will be treated or avoided. Device 20 can be used during a biopsy to provide an image of a needle being deployed into tissue. During a TIPS (transjugular intrahepatic portocaval shunt) procedure, an image can be produced to allow a physician to watch a needle being placed into the portal vein. For AAA (aortic abdominal aneurysm) graft delivery, device 20 can allow a physician to place a wire guide into a contralateral leg. Device 20 could also be used to image the location of a deployed implantable device both during and after deployment.

Although particular materials were highlighted herein for some components of device 20, those materials are not intended to be limiting of the types of materials which are suitable to be used in device 20. Additionally, where materials were not highlighted, a variety of materials could be used such as certain types of metals, polymers, ceramics or other types of materials which are suitable for use in devices for small body cavity applications.

Device 20 could also be used for a variety of other medical procedures and with a variety of other medical devices. Accordingly, the particular methods of use described herein are not indicative of any limiting aspects of the usage capabilities of device 20.

In the use of the term "rotation" (with respect to the rotation axis and motion about the pivot axis as well as generally), it should be understood that even though rotation often implies an angle change much greater than 360°, the devices disclosed herein may be configured in certain embodiments so that the rotational angle may rotate through angles less than 360°. In some instances the term "pivot" may be considered by some more natural than "rotate" or vice versa, but for the purposes of this application the terms "rotate" and "pivot" are used for clarity to indicate the axis about which a change in angle occurs, not the nature or magnitude of the angle change.

Many of the features described herein for the varying embodiments of device 20 can be used or interchanged with other embodiments of device 20 even when particular combinations of features were not specifically described, as would be understood by a person of ordinary skill in the art.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by the following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A medical device comprising:
   a catheter;
   a transducer positioned within the catheter, wherein the transducer is rotatable relative to the catheter along a rotation path about a rotation axis;
   a wire guide channel sized and configured to receive a wire guide; and
   a rotatable shaft extending substantially parallel to the rotation axis and rotatable about the rotation axis, wherein the shaft includes a conduit extending therethrough, wherein the wire guide channel extends through a cannula within the conduit, and wherein the transducer is operatively coupled with the rotatable shaft so that the transducer rotates in response to rotation of the rotatable shaft;
   wherein the transducer is rotatable around the wire guide channel.

2. The device of claim 1, wherein the transducer includes a first element and a second element, wherein the first element is positioned opposite to the second element with respect to the rotation axis, and wherein the channel extends between the first element and the second element.

3. The device according to claim 1, further comprising:
   a pivot mechanism rotatable about the rotation axis;
   a pivot member mounted to the pivot mechanism and pivotable about a pivot axis that is substantially perpendicular to the rotation axis, wherein the transducer is included in the pivot member.

4. The device according to claim 3, wherein the pivot member includes a magnetic layer, and further comprising a coil positioned concentric to the rotation axis, wherein the coil includes a plurality of electrically conductive windings, and wherein application of electric current to the coil creates a torque on the pivot member about the pivot axis.

5. The device according to claim 1, further comprising a microminiature motor positioned within the catheter, wherein operation of the microminiature motor rotates the transducer about the rotation axis.

6. The device according to claim 1, wherein a portion of the wire guide channel is in fluid communication with an area external to the catheter.

7. The device according to claim 1, wherein the transducer is formed in a crescent shape.

8. The device according to claim 3, further comprising a spring positioned to bias the pivot member.

9. The device according to claim 3, further comprising a conductor positioned within the pivot member to electrically connect the two elements of the transducer.

10. The device according to claim 1, further comprising a mounting piece having a cavity configured to hold the transducer.

11. The device according to claim 1, further comprising a mounting piece having a bore extending therethrough and a side passageway extending substantially radially relative to the bore.

12. The device according to claim 1, further comprising a mounting piece between two sections of a pivot member.

13. The device according to claim 3, wherein the pivot member has one section that includes the transducer and a second section that includes a magnetic layer.

14. The device according to claim 12, further comprising beamforming circuitry positioned within the mounting piece.

15. The device according to claim 1, further comprising a multiplexer and a demultiplexer positioned in a rotatable part of the device.

16. The device according to claim 1, further comprising a rotatable mounting piece including beamforming circuitry comprising a multiplexer and a demultiplexer.

17. The device according to claim 1, further comprising a beamforming transmitting circuit positioned on a rotatable part of the device.

18. The device according to claim 1, further comprising a beamforming receiving circuit positioned on a rotatable part of the device.

19. The device according to claim 1, further comprising a transducer backing and a beamforming circuit, wherein the beamforming circuit is integrated into the transducer backing.

20. A medical device comprising:
   a housing;
   a transducer positioned within the housing, wherein the transducer is rotatable relative to the housing along a rotation path about a rotation axis; and
   a wire guide channel sized and configured to receive a wire guide;
   a pivot mechanism rotatable about the rotation axis; and
   a pivot member mounted to the pivot mechanism and pivotable about a pivot axis that is substantially perpendicular to the rotation axis, wherein the transducer is included in the pivot member;
   wherein the transducer includes a first element and a second element, wherein the first element is positioned opposite to the second element with respect to the rotation axis, and wherein the channel extends between the first element and the second element; and
   wherein the second element is connected to the first element so that the second element pivots about the pivot axis in response to pivoting motion of the first element;
   wherein the transducer is rotatable around the wire guide channel.

* * * * *